United States Patent [19]

Kato et al.

[11] Patent Number: 4,986,892
[45] Date of Patent: Jan. 22, 1991

[54] OXYGEN SENSOR

[75] Inventors: Nobuhide Kato, Aichi; Masanori Katsu, Nagoya, both of Japan

[73] Assignee: NGK Insulators, Ltd., Japan

[21] Appl. No.: 517,701

[22] Filed: May 2, 1990

[30] Foreign Application Priority Data

May 15, 1989 [JP] Japan .................. 1-55571[U]

[51] Int. Cl.⁵ .......................................... G01N 27/409
[52] U.S. Cl. ...................................... 204/427; 204/428
[58] Field of Search ............ 204/427, 428, 429, 153.18

[56] References Cited

U.S. PATENT DOCUMENTS 4,189,355  2/1980  Fujishiro et al. ............... 204/427 X
4,668,375  5/1987  Kato et al. .......................... 204/426
4,784,743 11/1988  Iino et al. ........................... 204/425

Primary Examiner—G. L. Kaplan
Attorney, Agent, or Firm—Parkhurst, Wendel & Rossi

[57] ABSTRACT

An excellent oxygen sensor is provided, comprising; a sensor element having electrodes on inner and outer surfaces thereof, the electrode on the inner surface communicating to the atmosphere, and the electrode on the outer surface communicating to a gas to be measured; a metallic accommodating member accommodating the sensor element; and at least two airtight sealing portions arranged in the accommodating member for separating the gas to be measured from the atmosphere, at least one airtight sealing portion at the low temperature side of the oxygen sensor having a recessed portion formed under compression by pressing the outer surface of the metallic accommodating member after the formation of the airtight sealing portions by compressing the talc powder in the axial direction of the oxygen sensor. The oxygen sensor has splendid airtight sealing property of the airtight sealing portions containing compressed talc powders filled therein. Therefore, deterioration of the airtight sealing property of the airtight sealing portions can be substantially obviated and the life of the oxygen sensor can be prolonged, even when the oxygen sensor is exposed to vibrations and/or heat cycles during a long period of use.

1 Claim, 4 Drawing Sheets

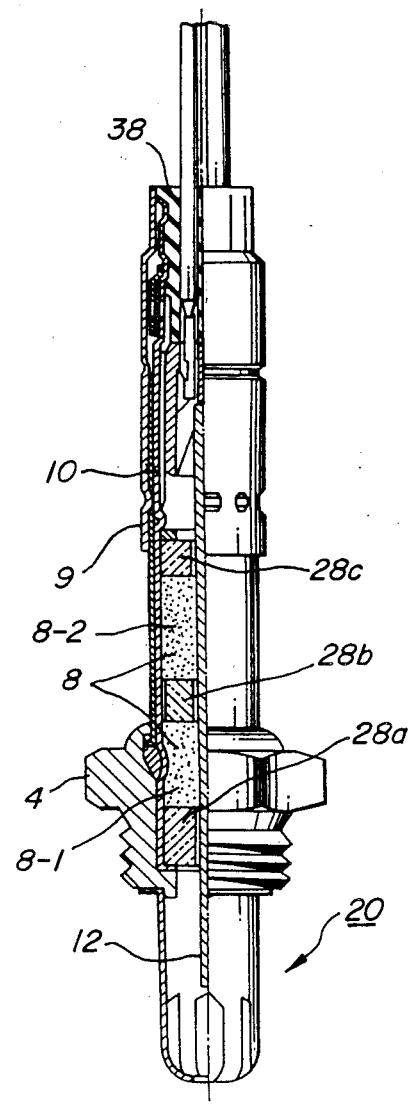
FIG. 4 *PRIOR ART*

OXYGEN SENSOR

BACKGROUND OF THE INVENTION

1. Field of the Invention

The present invention relates to an improvement of an oxygen sensor, comprising; a sensor element having electrodes on inner and outer surfaces thereof, the electrode on the inner surface communicating to the atmosphere, and the electrode on the outer surface communicating to a gas to be measured; a metallic accommodating member accommodating the sensor element; and at least two airtight sealing portions, arranged in the accommodating member for separating the gas to be measured from the atmosphere.

2. Related Art Statement

Heretofore, the above type of oxygen sensor is structured to separate the atmosphere from a gas to be measured, because the atmosphere is used as a standard oxygen gas. One way of separating the atmosphere from the gas to be measured is shown in FIG. 4, wherein talc powder 8 is filled in spaces defined by a metallic cap 10, a sensor element 12 and ceramic supporters 28a, 28b and 28c, and compressed in axial direction of the oxygen sensor under pressure to form an airtight sealing portion 8-1 at high temperature side of the oxygen sensor and an airtight sealing portion 8-2 at low temperature side of the oxygen sensor.

This type of oxygen sensor has a drawback in that the airtight sealing property of the sealing portions 8-1, 8-2 is gradually deteriorated due to vibrations and/or heat cycles of the oxygen sensor, though the sealing portions 8-1, 8-2 were compressed in axial direction under pressure. As a result, there arises a drawback in that the gas to be measured penetrates or invades in the standard oxygen atmosphere through the airtight sealing portions 8-1, 8-2 finally during a long period of use of the oxygen sensor to decrease the electromotive force of the oxygen sensor.

Regarding the drawback, a counterplan can be considered of increasing the compressing power in the axial direction to the talc powder to enhance the airtight sealing property of the sealing portions. However, in such a case, there arises another drawback in that due to an excessively high compressing power the metallic accommodating member is expanded to render the assembling of the oxygen sensor impossible or the ceramic supporters defining the airtight sealing portions are split.

SUMMARY OF THE INVENTION

Therefore, an object of the present invention is to obviate the above drawbacks and to provide an oxygen sensor which does not decrease its airtight sealing property even in a long period of use.

Another object of the present invention is to prevent the decrease of the airtight sealing property of the airtight sealing portions.

The present invention is an oxygen sensor, comprising; a sensor element having electrodes on inner and outer surfaces thereof, the electrode on the inner surface communicating to the atmosphere, and the electrode on the outer surface communicating to a gas to be measured; a metallic accommodating member accommodating the sensor element; and at least two airtight sealing portions arranged in the accommodating member for separating the gas to be measured from the atmosphere, at least one airtight sealing portion at the low temperature side of the oxygen sensor having a recessed portion formed under compression by pressing the outer surface of the metallic accommodating member after the formation of the airtight sealing portions by compressing the talc powder in the axial direction of the oxygen sensor.

By this arrangement, at least one airtight sealing portion at the low temperature side of the oxygen sensor has a recessed portion, so that the pressing power in the radial direction of the oxygen sensor can be enlarged by the volume decrease of the airtight sealing portion resulting from the formation of the recessed portion, even when the pressing power in the axial direction is the same as usual at the time of forming the airtight sealing portions. Therefore, the talc powder filled in the airtight sealing portions can be compressed more densely by the enlarged pressing power, so that the deterioration of the airtight sealing property of the airtight sealing portions can be decreased substantially, even when the oxygen sensor is exposed to vibrations and/or heat cycles for a long period of use.

The reason why the recessed portion is formed on at least one airtight sealing portion at the low temperature side of the oxygen sensor is because the formation of the recessed portion on the airtight sealing portion at the high temperature side of the oxygen sensor has little effect of preventing the decrease of the airtight sealing property of the airtight sealing portions, which the present invention aimed to achieve. Of course, the effect of preventing the decrease of the airtight sealing property of the airtight sealing portions can be made maximum, if the recessed portion is provided on all of the airtight sealing portions.

The timing of forming the recessed portion should be after the formation of the airtight sealing portions by compressing the talc powder in the axial direction of the oxygen sensor, because airtight sealing property equal to that of usual oxygen sensors can be merely obtained, if the timing of forming the recessed portion is before the formation of the airtight sealing portions by compressing the talc powder in the axial direction of the oxygen sensor.

BRIEF DESCRIPTION OF THE DRAWINGS

For a better understanding of the present invention, reference is made to the accompanying drawings, in which:

FIG. 4 is a partial crosssectional view of an example of a prior oxygen sensor.

Throughout different views of the drawings, 4 is a housing, 8, 8-1 and 8-2 are talc powder, 9 is a metal boot, 10 is a metal cap, 11 is a caulking, 12 is a sensor element, 13 is an airtight ring, 14 is lead wires, 15 is a rubber stopper, 16 is a recessed portion, 20 is an oxygen sensor, 22 is a sensor element, 24 is a housing, 26 is an inner cylinder, 28a, 28b and 28c are ceramic supporters, 30a and 30b are talc powder, 32 is an outer cylinder, 34 is an upper circular projection of the housing 24, 36 is lead wires, and 38 is a rubber plug.

DESCRIPTION OF THE PREFERRED EMBODIMENTS

Hereinafter, the present invention will be explained in detail with reference to Examples.

Figure 1:
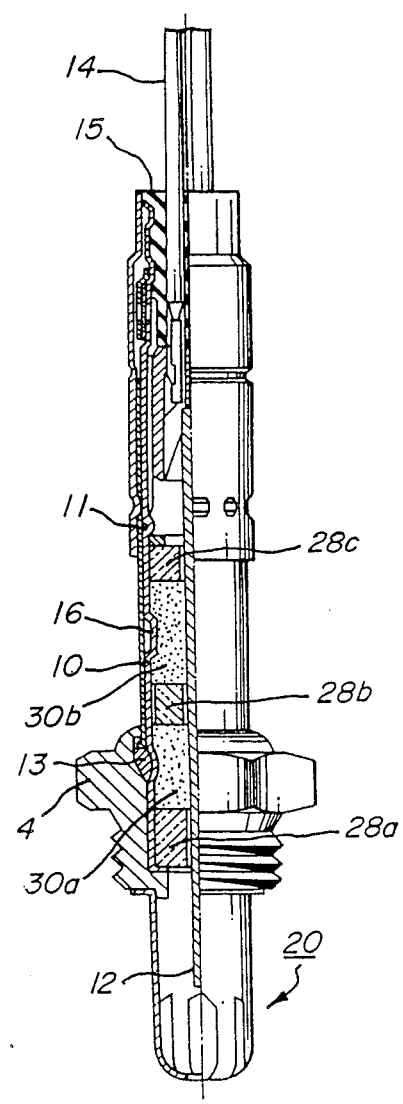
FIG. 1 is a partial crosssectional view of an example of the present oxygen sensor.

Referring to FIG. 1 showing an embodiment of the present invention, the oxygen sensor 20 has a plate-shaped sensor element 12 which is accommodated in a cylindrical metallic cap 10 via ceramic supporters 28a, 28b and 28c and fixed and airtightly sealed by talc powders 30a and 30b filled and compressed between the ceramic supporters 28a, 28b and 28c in the cap 10. The fixing of the sensor element 12 by means of the talc powder 30 is achieved by compressing the talc powder 30 in the axial direction of the oxygen sensor, and a caulking 11 serves to confine the compression of the talc powder 30 a and 30b in the upward direction of the oxygen sensor 20. The compressed talc powder 30a forms an airtight sealing portion at the high temperature side of the oxygen sensor 20, and the compressed talc powder 30b forms an airtight sealing portion at the low temperature side of the oxygen sensor.

According to the present invention, a recessed portion 16 is formed on the airtight sealing portion containing the compressed talc powder 30b at the low temperature side of the oxygen sensor 20 by pressing the outer surface of the metallic cap 10 to compress the talc powder 30b further so as to improve the airtight sealing property of the airtight sealing portion at the low temperature side of the oxygen sensor.

Meanwhile, a rubber plug 15 having lead wires 14 inserted therein is fixed by caulking the metallic cap 10 at the upper open end portion of the cap 10, and the other end of the metallic cap 10 is fixed in a housing 4 via an airtight ring 13, so that the cap 10 is closely sealed. The lead wires 14 are electrically connected at their ends to terminal electrodes of the sensor element 12.

The oxygen sensor constructed as mentioned above has improved density of the talc powder due to the compression of the talc powder 30b by the formation of the recessed portion 16 on the airtight sealing portion at the low temperature side of the oxygen sensor formed by pressing the cap 10 from the exterior, so that the deterioration of the airtight sealing property of the compressed talc powder can be prevented substantially, even when the oxygen sensor is exposed to vibrations and/or heat cycles during a long period of use.

Figure 2:
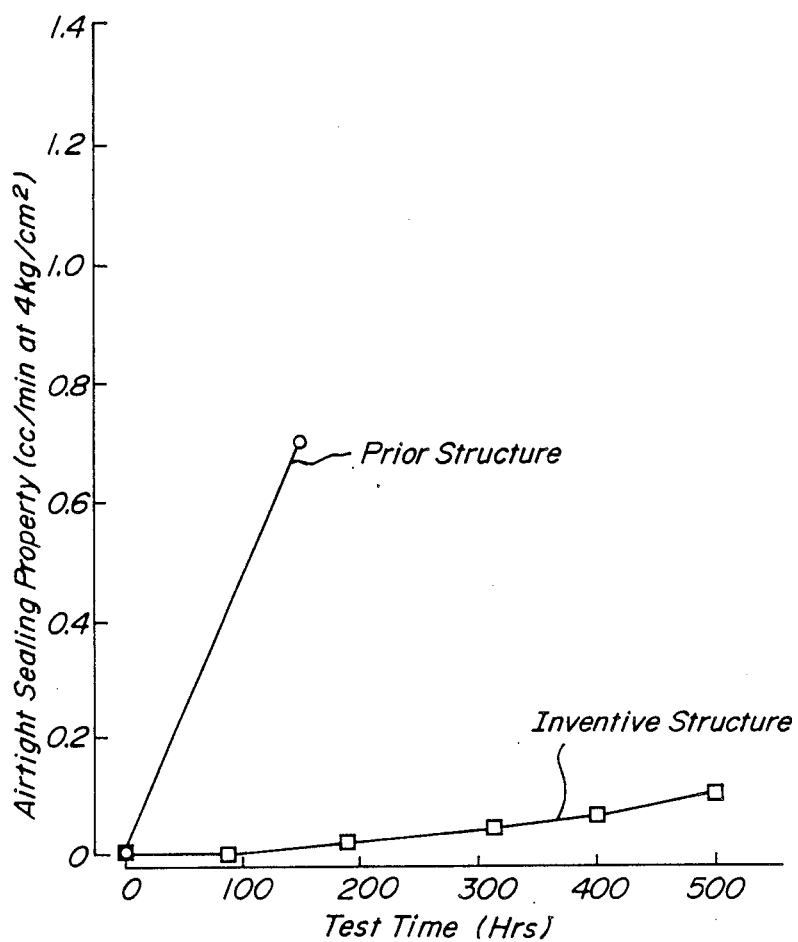
FIG. 2 is a characteristic graph of a relation between the airtight property and tested hours under heat cycles and vibrations.

A prior oxygen sensor and the present oxygen sensor are tested for comparison in a vibration heat cycle test to study the decrease of the airtight sealing property of the compressed talc powder. The results are shown in the attached FIG. 2. The tests are conducted in a vibration heat cycle condition of a vibration frequency of 50–250 Hz (30 min. sweep), a vibration acceleration of 30–50 G, and a heat cycle of repetitions of 900° C.×30 min. and room temperature×25 min. The airtight sealing property of the talc powders is determined by measuring an amount of air that passed both the talc powders 30a and 30b, using a compressed air of a pressure of 4 kg/cm$^2$. As seen clearly from FIG. 2, the decrease of the airtight sealing property of the talc powder can be substantially obviated by adopting the structure of the present oxygen sensor.

Figure 3:
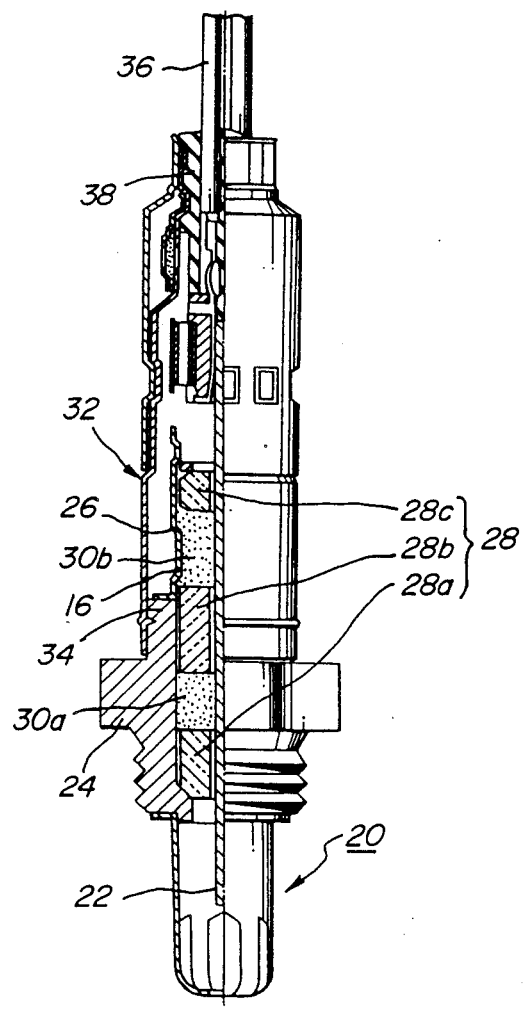
FIG. 3 is a partial crosssectional view of another example of the present invention.

Referring to FIG. 3 showing another embodiment of the present invention, the oxygen sensor 20 has a plate-shaped sensor element 22 which is accommodated in a metallic housing 24 and a cylindrical metallic inner cylinder 26 welded thereto via ceramic supporters 28a, 28b and 28c and fixed and airtightly sealed by talc powders 30a, 30b filled and compressed between the ceramic supporters 28a, 28b and 28c in the metallic housing 24 and the connected metallic inner cylinder 26. The compressed talc powder 30a forms an airtight sealing portion at the high temperature side of the oxygen sensor, while the compressed talc powder 30b forms an airtight sealing portion at the low temperature side of the oxygen sensor.

According to the present invention, a recessed portion 16 is formed on the airtight sealing portion containing the compressed talc powder 30b at the low temperature side of the oxygen sensor 20 by pressing the outer surface of the inner cylinder 26 to compress the talc powder 30b further so as to improve the airtight sealing property of the airtight sealing portion at the low-temperature side of the oxygen sensor.

In this embodiment, in order to protect the sensor element 22 from outer environment, a metallic outer cylinder 32 is fitted to the outer circumferential surface of the upper portion of the housing 24 having a circular projection 34, and welded and airtightly fixed to the circumferential surface of the upper portion of the housing 24 over the entire lower periphery thereof. Meanwhile, the upper open end of the outer cylinder 32 opposite to the lower end of the outer cylinder 32 which fits to the housing 24 receives a rubber plug 38 fitted therein receiving lead wires 36 inserted therein. The rubber plug 38 is caulked and fixed by the outer cylinder 32 to closely seal the same. The lead wires 36 are electrically connected at their ends to the electrode terminal of the sensor element 22.

Both the abovementioned embodiments have two airtight sealing portions, however, they can have three or more airtight sealing portions. In any case, the desired effect of preventing the airtight sealing property of the airtight sealing portions can be achieved, if at least one airtight sealing portion at the low temperature side of the oxygen sensor is compressed to form a recessed portion by pressing the outer surface of the metallic accommodating member accommodating the talc powder which surrounds the sensor element.

As apparent from the foregoing explanations, the oxygen sensor of the present invention has a recessed portion which compresses the talc powder at at least one airtight sealing portion at the low temperature side of the oxygen sensor, which recessed portion being formed by pressing the outer surface of the metallic accommodating member accommodating the talc powder surrounding the sensor element after the formation of the airtight sealing portions by compressing the talc powder in the axial direction of the oxygen sensor, so that the present oxygen sensor has improved splendid airtight sealing property of the airtight sealing portions containing compressed talc powders filled therein as compared with that of prior oxygen sensor. As a result, the deterioration of the airtight sealing property of the airtight sealing portions can be substantially obviated and the life of the oxygen sensor can be prolonged, even when the oxygen sensor is exposed to vibrations and/or heat cycles during a long period of use.

Although the present invention has been explained with specific embodiments, it is of course apparent to those skilled in the art that various changes and modifications are possible without departing from the broad spirit and aspect of the present invention as defined in the appended claims.

What is claimed is:

1. An oxygen sensor comprising a sensor element having electrodes on inner and outer surfaces thereof, the electrode on the inner surface communicating to the atmosphere, and the electrode on the outer surface communicating to a gas to be measured; a metallic accommodating member accommodating the sensor element; and at least two airtight sealing portions of powder arranged in the accommodating member for separating the gas to be measured from the atmosphere, at least one airtight sealing portion at the low temperature side of the oxygen sensor having a recessed portion formed under compression by pressing the outer surface of the metallic accommodating member after the formation of the airtight sealing portions by compressing the powder in the axial direction of the oxygen sensor.

* * * * *